(12) United States Patent
Fell

(10) Patent No.: US 8,080,059 B2
(45) Date of Patent: Dec. 20, 2011

(54) SURGICALLY IMPLANTABLE PROSTHESIS WITH ACTIVE COMPONENT

(76) Inventor: Barry M. Fell, Hummelstown, PA (US)

( * ) Notice: Subject to any disclaimer, the term of this patent is extended or adjusted under 35 U.S.C. 154(b) by 189 days.

(21) Appl. No.: 12/160,680

(22) PCT Filed: Jan. 15, 2007

(86) PCT No.: PCT/US2007/060543
§ 371 (c)(1),
(2), (4) Date: Jul. 11, 2008

(87) PCT Pub. No.: WO2007/084878
PCT Pub. Date: Jul. 26, 2007

(65) Prior Publication Data
US 2009/0012615 A1    Jan. 8, 2009

Related U.S. Application Data

(60) Provisional application No. 60/758,739, filed on Jan. 13, 2006.

(51) Int. Cl.
*A61F 2/08* (2006.01)
*A61F 2/38* (2006.01)

(52) U.S. Cl. .......... 623/14.12; 623/20.14; 623/20.3

(58) Field of Classification Search .......... 623/14.12, 623/20.14–20.36
See application file for complete search history.

(56) References Cited

U.S. PATENT DOCUMENTS

| | | | |
|---|---|---|---|
| 5,032,129 A | 7/1991 | Kurze et al. | |
| 5,176,907 A | 1/1993 | Leong | |
| 5,681,289 A * | 10/1997 | Wilcox et al. | 604/175 |
| 5,876,446 A | 3/1999 | Agrawal et al. | |
| 6,071,982 A | 6/2000 | Wise et al. | |
| 6,110,209 A | 8/2000 | Stone | |
| 6,206,927 B1 | 3/2001 | Fell | |
| 6,303,136 B1 | 10/2001 | Li et al. | |
| 6,344,061 B1 | 2/2002 | Leitao et al. | |
| 6,355,705 B1 | 3/2002 | Bond et al. | |
| 6,544,090 B1 | 4/2003 | Anderson et al. | |
| 6,558,421 B1 | 5/2003 | Fell et al. | |
| 6,582,715 B1 | 6/2003 | Barry et al. | |
| 6,602,975 B2 | 8/2003 | Hubbell et al. | |
| 6,635,268 B2 | 10/2003 | Peery et al. | |

(Continued)

FOREIGN PATENT DOCUMENTS

WO    WO 03049650 A1 * 6/2003

(Continued)

OTHER PUBLICATIONS

International Search Report for PCT/US2007/060543 dated Jan. 6, 2007.

*Primary Examiner* — David H Willse
*Assistant Examiner* — Javier Blanco
(74) *Attorney, Agent, or Firm* — Brooks Kushman P.C.

(57) ABSTRACT

A prosthesis for surgical implantation into a knee joint compartment between a femoral condyle and its corresponding tibial plateau includes a body including a bottom face, an opposed top face, and a peripheral edge extending between the top and bottom faces. The body has a first portion and at least one second portion, wherein at least one second portion is configured to store and release at least one active component into the knee joint compartment without degradation of the mechanical function of the prosthesis.

22 Claims, 3 Drawing Sheets

U.S. PATENT DOCUMENTS

| | | |
|---|---|---|
| 6,692,760 B2 | 2/2004 | Miyamoto et al. |
| 6,713,293 B1 | 3/2004 | Grummt et al. |
| 6,719,989 B1 | 4/2004 | Matsushima et al. |
| 6,855,165 B2 | 2/2005 | Fell |
| 6,866,684 B2 | 3/2005 | Fell |
| 6,911,044 B2 | 6/2005 | Fell |
| 6,923,831 B2 | 8/2005 | Fell |
| 6,966,928 B2 | 11/2005 | Fell |
| 7,297,161 B2 | 11/2007 | Fell |
| 7,338,524 B2 | 3/2008 | Fell et al. |
| 7,341,602 B2 | 3/2008 | Fell et al. |
| 2002/0018798 A1 | 2/2002 | Sewing et al. |
| 2003/0008396 A1 | 1/2003 | Ku |
| 2004/0064193 A1 | 4/2004 | Evans et al. |
| 2004/0142013 A1 | 7/2004 | Rubsamen |
| 2004/0180072 A1 | 9/2004 | Tunc et al. |
| 2005/0278025 A1 | 12/2005 | Ku et al. |
| 2006/0047341 A1 * | 3/2006 | Trieu .................. 623/17.12 |

FOREIGN PATENT DOCUMENTS

| | | |
|---|---|---|
| WO | WO 2005/107647 | 11/2005 |

* cited by examiner

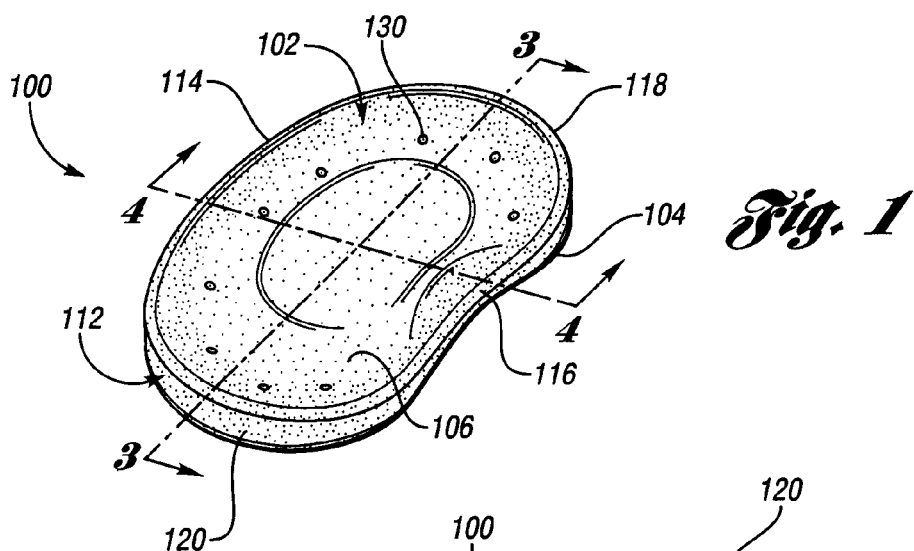
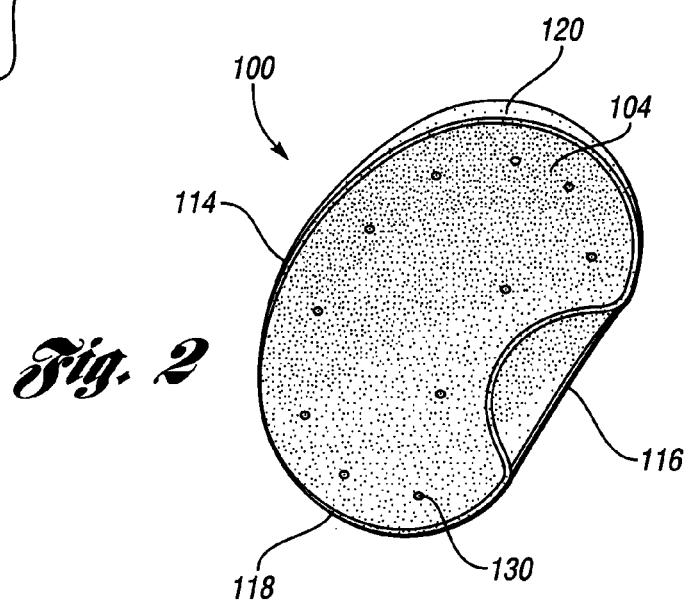
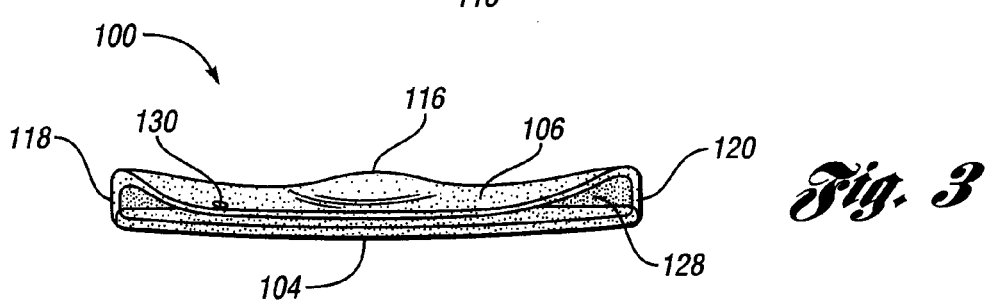
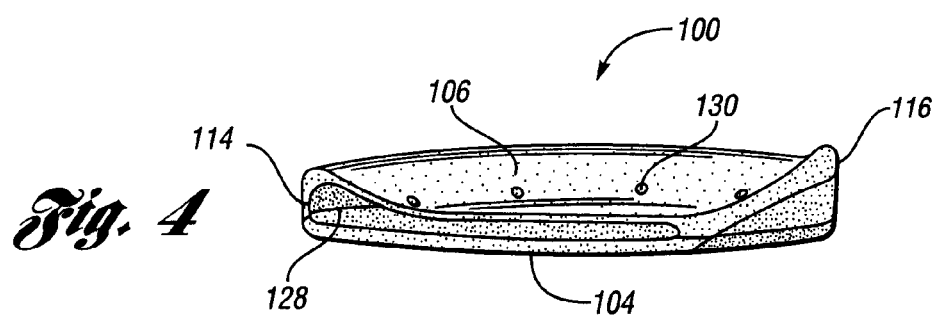

SURGICALLY IMPLANTABLE PROSTHESIS WITH ACTIVE COMPONENT

CROSS-REFERENCE TO RELATED APPLICATIONS

This application claims the benefit of U.S. provisional application Ser. No. 60/758,739 filed Jan. 13, 2006.

BACKGROUND OF THE INVENTION

1. Field of the Invention

This invention relates to a surgically implantable prosthesis having an active component.

2. Background Art

Structural implants for the augmentation or replacement of body components are generally single purpose in their design and function. That is, they are designed to provide a substantially equivalent, functional replacement for a component of the body that is missing or worn out due to injury or disease, without additional functionality.

BRIEF DESCRIPTION OF THE DRAWINGS

FIG. 1 is a top perspective view of a prosthesis according to an aspect of the present invention;

FIG. 2 is a bottom perspective view of the prosthesis of FIG. 1;

FIG. 3 is a cross-sectional view of the prosthesis of FIG. 1 taken along line 3-3;

FIG. 4 is a cross-sectional view of the prosthesis of FIG. 1 taken along line 4-4;

DETAILED DESCRIPTION OF THE INVENTION

Figure 5:
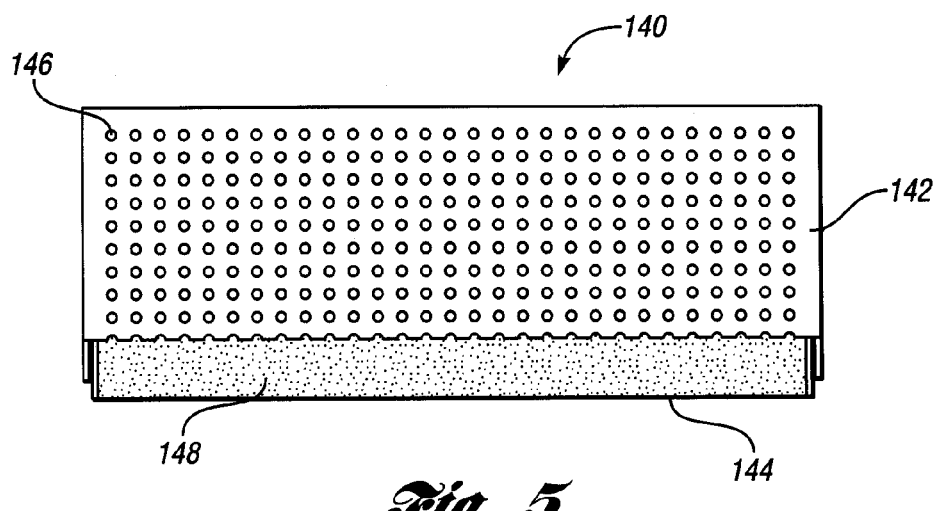
FIG. 5 is top perspective view, partially cut away, of a pump structure in accordance with an aspect of the present invention.

As required, detailed embodiments of the present invention are disclosed herein; however, it is to be understood that the disclosed embodiments are merely exemplary of the invention that may be embodied in various and alternative forms. The figures are not necessarily to scale, and some features may be exaggerated or minimized to show details of particular components. Therefore, specific structural and functional details disclosed herein are not to be interpreted as limiting, but merely as a representative basis for teaching one skilled in the art to variously employ the present invention.

The present invention includes a surgically implantable prosthesis, such as an orthopedic or other load-bearing prosthesis, which may be configured to incorporate and release a pharmacologically or biologically active component. As used herein, the term "active component" is understood to include any substance or material, or combination of substances and materials, which may have a pharmacological or biological effect or the like. The prosthesis according to the present invention cooperates with an active component to provide additional properties or functions without a degradation of the structural or mechanical functions of the prosthesis. This is in contrast to most prior art devices which rely on bio-resorption that eventually leads to the destruction of the prosthesis, such that unless a 1:1 ratio of cellular regrowth to substrate/carrier degradation exists, prior art devices cannot be fully functional throughout the regrowth process.

The prosthesis according to the present invention is designed to be surgically implantable into a body joint to replace damaged tissue therein. The prosthesis may be configured as a unicompartmental device suitable for minimally invasive, surgical implantation into a knee compartment requiring little or no bone resection. The knee compartment is defined by the space between a femoral condyle and the respective tibial plateau, in which a portion of the natural meniscus is ordinarily located, wherein the term "unicompartmental" refers to either the medial or lateral compartment. However, it is understood that the prosthesis could be utilized in joints other than the knee such as, but not limited to, the hip, shoulder, wrist, thumb, toe, ankle, or elbow.

The prosthesis according to the present invention may be translatable, such that during natural articulation of the knee joint the prosthesis is allowed to move or change its lateral/medial and/or anterior posterior position relative to the tibial plateau. The prosthesis may also be self-centering, such that upon translation from a first position to a second position during knee articulation, the prosthesis will return to substantially its original position as the articulation of the knee joint is reversed and the original knee position is reached. Alternatively, the prosthesis may be fixed. By effectively replacing worn articular material, the prosthesis of the present invention may restore a more normal joint alignment, improve joint stability, and provide a smooth bearing surface against which the femoral condyle can articulate.

With reference first to FIG. 1, a prosthesis according to an aspect of the present invention is illustrated and designated generally by reference numeral 100. Prosthesis 100 includes a body 102 having a bottom, or tibial, face 104 and an opposite top, or femoral, face 106. According to one aspect of the present invention, bottom face 104 may include a generally convex surface and top face 106 may include a generally concave surface. However it is understood that other contours of bottom face 104 and top face 106 ranging from generally convex to generally flat to generally concave are fully contemplated in accordance with the present invention. It is also understood that the terms "concave" and "convex" as used herein are not restricted to describing surfaces with a constant radius of curvature, but rather are used to denote the general appearance of the surfaces.

Body 102 further includes a peripheral edge 112 extending between bottom face 104 and top face 106 and having a first side 114, a second side 116 opposite first side 114, a first end 118, and a second end 120 opposite first end 118. As shown, edges along the periphery of prosthesis 100 may be rounded. As shown, body 102 may have a generally elliptical shape in plan. It is understood that the term "generally elliptical" as used herein is intended to include all construction methods which yield a generally planar shape which is longer in one direction than in the transverse direction and has rounded corners. However, prosthesis 100 is not limited to any particular shape.

According to one aspect of the present invention, prosthesis 100 may comprise a relatively hard, relatively high modulus material. Suitable materials include, for example, metals such as steel or titanium, metal alloys, ceramics, and reinforced and non-reinforced thermoset or thermoplastic polymers. It is understood that the term "hard" as used herein is used to describe a material that may be sufficient to span defects in the tibia or femur without substantially deforming into the defects, allowing for the provision of recessed or non-contacting areas of the prosthesis. In this way, damaged areas may not be subjected to static and dynamic loading and wear, thereby increasing the opportunity for the body's natural regenerative capability to function. The prosthesis of the present invention may redistribute the load to healthy tissue, spanning areas of imperfection and allowing inflamed, diseased, or other damaged areas to regenerate. Of course, it is understood that the prosthesis could alternatively be constructed from softer materials, such as a hydrogel material.

Prosthesis 100 need not be made only of a single material, but composite structures may also be used. Materials could include elastomeric polymers such as nylon, silicone, polyurethane, polypropylene, polyester, or the like, optionally fiber-reinforced, or viscous-elastic materials such as hydrogels, as well as other hydrophilic materials or hydrophobic materials. Materials, such as biocompatible polymers, capable of containing living cells could also be utilized.

Active components may be provided within prosthesis 100 of the present invention in a number of ways. For example, an active component may be incorporated in a coating, such as an adhesive or powder spray type, applied to the surface of prosthesis 100. A surface coating may be placed on a weight-bearing (e.g., articulating) surface of prosthesis 100, on a non-functional surface (e.g., peripheral surface) of prosthesis 100, or on any other surface of prosthesis 100. The active component may be dispensed via abrasion of a surface of prosthesis 100, may be released by diffusion through the prosthesis material, or may also be released as the bond between the active component and prosthesis material is cleaved. The surface coating may be applied by any process, such as by subjecting the prosthesis to a surface treatment until a desired surface roughness is obtained. The roughened surface may then be exposed to precipitation of the surface coating. An active component may also be electroplated onto prosthesis 100. Of course, other methods of applying surface coatings are fully contemplated according to the present invention.

According to another aspect of the present invention, prosthesis 100 could include an active component impregnated therein, wherein the porosity of the material from which prosthesis 100 is constructed may control the quantity and release rate of the active component. In order to embed the active component into prosthesis 100, any one of a powder, aqueous solution, or suspension of the active component can be combined with the prosthesis material. The active component may also be introduced into prosthesis 100 by placing prosthesis 100 into a bath containing an aqueous solution of the active component and allowing the active component to diffuse into the prosthesis material. The active component may be bound (e.g., chemically) to the material of prosthesis 100, or may be physically dispersed with the material of prosthesis 100. The active component may be released by diffusion through the prosthesis material, may be released as the bond between the active component and prosthesis material is cleaved, or may be dispensed via abrasion of a surface of prosthesis 100.

Suitable materials for the construction of prosthesis 100 include, but are not limited to, porous ceramic, metal, polymeric, or hydrogel materials which can leach an active component over time while maintaining the structural functions and physical shape of prosthesis 100. The material may be selected to include a pore size specificity which includes an osmotic membrane function to limit cell or protein transfer by direction as well as a means of protecting the active component from destruction by cellular attack. In one embodiment, the active component may include piezoelectric crystals embedded within prosthesis 100, such as to supply an electromagnetic field pulse, which may provide an improved environment to promote articular cartilage growth.

According to another aspect of the present invention, an active component may be contained within a carrier, which may be biodegradable, that is disposed within prosthesis 100. For example, following surgery, 20 mg of sodium hyaluronate in 2 ml of water (Hyalgan®) is typically administered to a patient via injection (e.g., 3 to 5 injections at weekly intervals). The equivalent dosage may be administered by placing the sodium hyaluronate in a carrier which is designed to deliver a reduced dosage in a continuous fashion via prosthesis 100 according to the present invention, resulting in less inflammation of the joint and less patient discomfort.

Suitable materials for carriers include metallic materials, such as coated metals, where active components may be present on the outside surfaces. If porous metals are utilized, active components may be contained within pores built into the material. Polymeric materials, such as polyurethane, which are biocompatible and biodegradable, may alternatively be utilized. Photopolymerizable biodegradable hydrogels, PVA (polyvinyl alcohol) hydrogels, and other such materials may be used in accordance with the present invention as tissue-contacting materials and controlled-release carriers.

According to an aspect of the present invention depicted in FIGS. 1-4, an active component may be contained internally within prosthesis 100, such as within an internal cavity 128 (see FIGS. 3 and 4). In this case, the active component may be distributed through bleed holes 130 to the outside of prosthesis 100. Bleed holes 130 may be provided on both bottom face 104 and top face 106 as shown, or alternatively may be provided on top face 106 only, on bottom face 104 only, or on peripheral edge 112. Bleed holes 130 may be of any size or number suitable for a particular active component, may use a size selective passage of materials, and may exhibit osmotic behavior. As such, the configuration of bleed holes 130 may be used to provide tight control on the release of a particular active component for a particular therapeutic need. Still further, an active component may be contained within microballoons which may be formed integrally with the structural material of the prosthesis.

Figure 6:
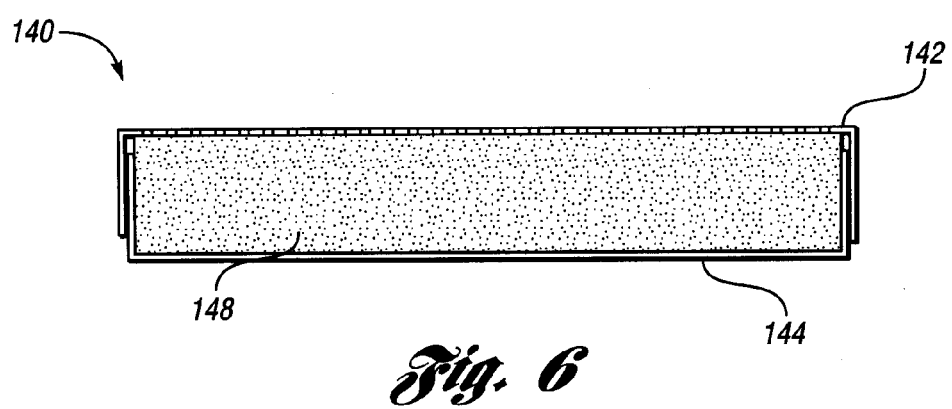
FIG. 6 is a front elevational view of the pump structure of FIG. 5.

As shown in FIGS. 5 and 6, prosthesis 100 may include a mechanical pump structure 140 which may aid in dispensing an active component. Pump structure 140 may include a top member 142 and a bottom member 144 which may nest within and are movable with respect to each other. Top member 142, bottom member 144, or both may include holes 146 for releasing the active component, and top and bottom members 142, 144 may be formed from any suitable material. An inner material 148, such as a gel or sponge-like material, may be disposed between top member 142 and bottom member 144. Forces acting on prosthesis 100 may cause relative movement of top and bottom members 142, 144, which then may act as a mechanical pump to compress inner material 148 and dispense the active component therefrom. It is understood that pump structure 140 may be disposed within prosthesis 100 such that it is surrounded by body 102, or that top member 142 and bottom member 144 may comprise top face 106 and bottom face 104 of prosthesis 100, respectively. As such, pump structure 140 may have any size, shape, or configuration necessary for either implementation.

Figure 7:
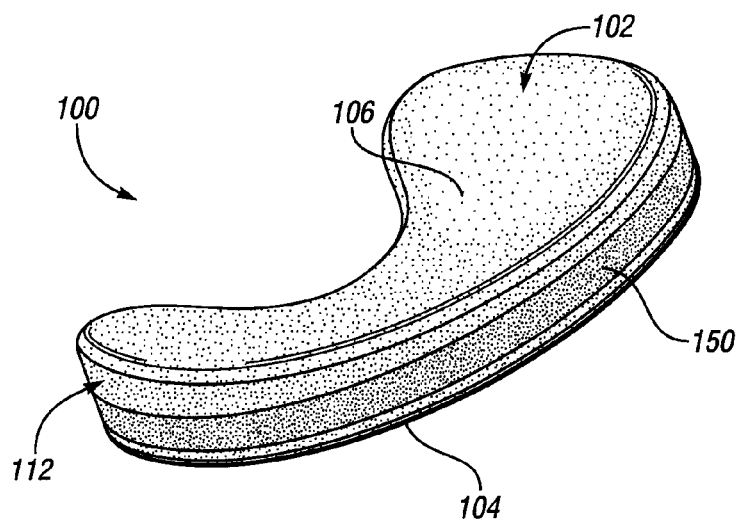
FIG. 7 is a top perspective view of a prosthesis having an indentation for containing an active component according to an aspect of the present invention.

With reference to FIG. 7, according to another aspect of the present invention, an active component may be contained within a concavity or depression of prosthesis 100. In one embodiment, the depression may be disposed in an area of prosthesis 100 that is not configured to contact any opposing load-bearing or functional surface, but that would have contact with body fluids for transfer of the active components, such that active components may not be dissipated too quickly. For example, the depression may have the form of a groove 150 or other indentation formed within a non-weight bearing portion of prosthesis peripheral edge 112 which is capable of containing and releasing an active component. The depression may be integrated into prosthesis 100, and thus contained within the primary material of prosthesis 100 itself. Alternatively, the depression could be provided in a secondary material. It is understood that the remainder of prosthesis 100 may also be configured to contain and release an active component. It is also understood that the loss of the active component in the process of performing its intended duties may or may not result in a change to the outer physical dimensions of prosthesis 100. Entire prosthesis 100 or only just a portion thereof may be left in an entirely porous state after the period of activity is concluded.

Figure 8:
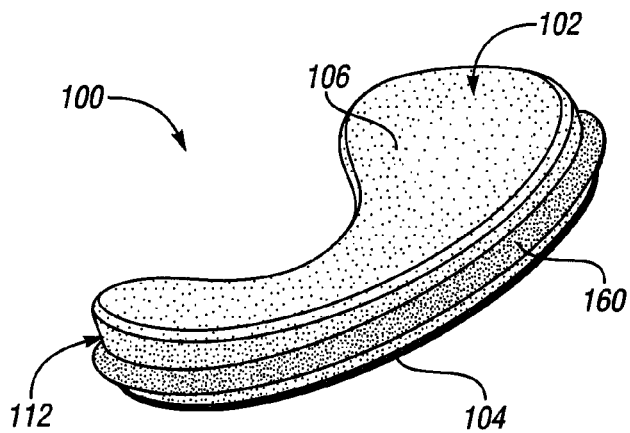
FIG. 8 is a top perspective view of a prosthesis having a temporary member for containing an active component according to an aspect of the present invention.

Prosthesis 100 according to the present invention may include at least one temporary member which may be designed to degrade or be removed after a period of therapeutic function. For example, as shown in FIG. 8, prosthesis 100 may include a pad 160, such as constructed of alginate fibers, which holds the active component for use immediately after reconstructive surgery. Pad 160 may not be weight-bearing, and instead located on a non-functional surface of prosthesis 100, such as peripheral edge 112, to secrete active components during the regeneration process. Alternatively, pad 160 could be disposed in a load-bearing location on prosthesis 100. It is understood that a pad 160 or other temporary portion of prosthesis 100 having any location, size, shape, or material composition is fully contemplated. As an example of the use of pad 160, after cartilage graft transplantation, HA, growth factors, or other materials conducive to facilitating the success of the graft could be placed within the joint capsule in a pad 160 that secretes active component at a prescribed rate into the joint capsule over a pre-determined period of time.

According to another aspect of the present invention, a majority or even the entirety of prosthesis 100 could be constructed as a temporary member. In this case, prosthesis 100 may provide an initial mechanical or physical function along with its active function, where prosthesis 100 may be designed to be partially or totally resorbed by the body after a prescribed period of time. In this manner, prosthesis 100 can provide a temporary structural and active function, for example, providing a protective layer over an area of cartilage transplantation, wherein prosthesis 100 may be designed to be resorbed once the cartilage is safely grown in.

Figure 9:
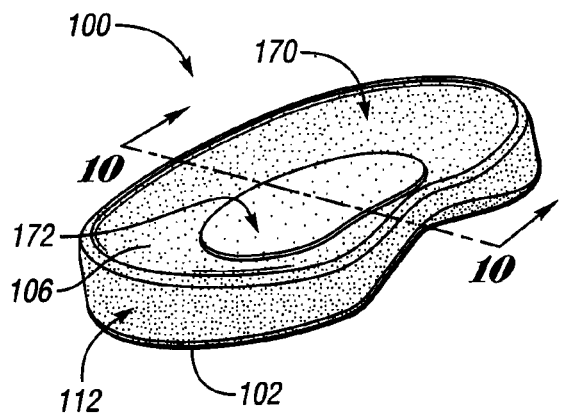
FIG. 9 is a top perspective view of a prosthesis having a second portion for release of an active component according to an aspect of the present invention.
Figure 10:
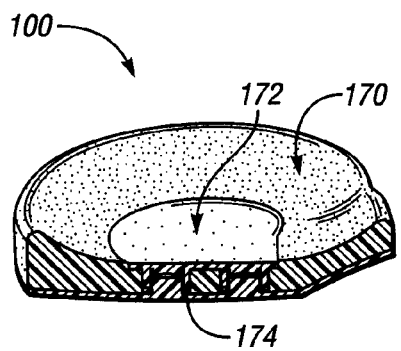
FIG. 10 is a cross-sectional view of the prosthesis of FIG. 9 taken along line 10-10.

Turning now to FIGS. 9 and 10, prosthesis 100 may include a first portion 170 and at least one second portion 172, wherein second portion 172 may provide a functional surface of prosthesis 100 as well as providing the capability to release an active component. For example, in the case of a knee prosthesis, second portion 172 may perform a meniscal function or otherwise provide a load-bearing or functional surface, and also be configured to house active components. Second portion 172 may be mechanically (e.g., snap fit), chemically, or otherwise attached to first portion 170 to form prosthesis 100, and first and second portions 170, 172 can be constructed from the same or different materials. Second portion 172 can include a reservoir 174 of any configuration suitable to dispense active component(s), or may have active component(s) embedded therein, applied as a surface coating, or include and release active components via any other method. Although second portion 172 is depicted herein as being centrally located and surrounded by first portion 170, it is understood that first and second portions 170, 172 are not limited to this particular size and configuration. First portion 170 may also be configured to contain and release an active component.

Figure 11:
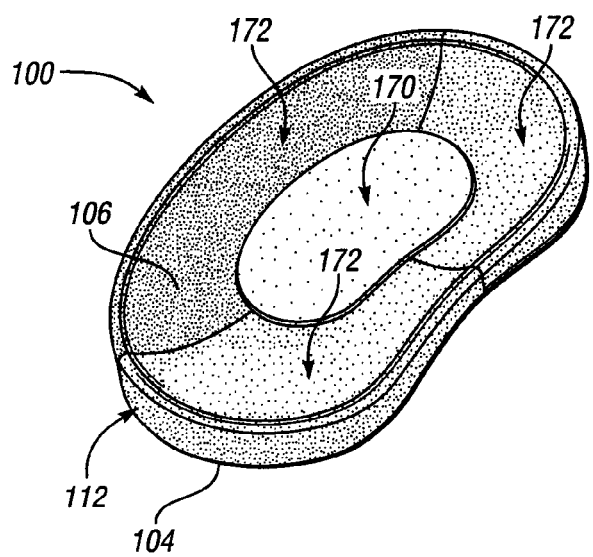
FIG. 11 is a top perspective view of a prosthesis having multiple second portions for release of an active component according to an aspect of the present invention.

As shown in FIG. 11, prosthesis 100 according to the present invention may include two or more second portions 172 which allow for sequential, differential, or simultaneous dispersion of active components. The multiple second portions 172 could have reservoirs for containing active components, could have an active component embedded therein, or contain an active component in any manner for release by any mechanism. In one example, second portions 172 could be constructed of the same material, but contain different active components. As another example, second portions 172 could be constructed of different materials, but contain the same active component, perhaps for releasing at different rates. However, it is understood that any combination of materials and active components for the different second portions 172 are fully contemplated. Second portions 172 can also have any number, size, or location within prosthesis 100. Again, first portion 170 may also be configured to contain and release an active component.

The active component may be dispensed from prosthesis 100 at once or on a time release basis, either short term or sustained release. As described above, the active component may be dispensed through bio-absorption without degradation of the structural and other functions of prosthesis 100. After implantation of prosthesis 100, the active component could be replenished within prosthesis 100 through injection, pumping or other means from outside the skin surface.

According to the present invention, the additional properties and functions afforded by the active component may include an analgesic function, such as providing anti-inflammatory action. An anesthetic function could be provided, such as to manage and lower short-term pain, for example, post-operative pain. The anesthetic function could also be used for long term pain management. Another function provided by the active component could be promotion of a healthier body or joint environment, wherein an active component may be provided in the form of additional nutrients and other chemicals that promote healthy cell growth, such as the growth of bone or cartilage. Nutrients and chemicals could also be provided to promote the regrowth of articular materials in order to restore the articulating surface of the joint. Promoting the rate and quality of desired tissue regrowth lowers the rejection rate of an implant particularly when tissue and bone growth is desirable.

Furthermore, unhealthy cellular, enzymatic, protein, and other activity may be diminished by providing an active component in the form of additional inhibitors to the implant environment. Such inhibitors may suppress undesirable cell or chemical production that would normally lead to further joint degradation. This is particularly useful when prosthesis 100 leaves components of the joint untouched. This approach may prevent fibrotic overgrowth which can lead to joint immobility, and also may inhibit destructive enzyme production such as matrix metalloproteinases (MMP's) that affect cartilage destruction. Still further, prosthesis 100 according to the present invention can facilitate proper joint function by providing an active component which includes additional lubrication to a joint environment, thereby improving the mechanical function of the joint, reducing wear and the formation of wear debris (e.g., reducing the occurrence of osteolysis), and thus extending the life of the prosthesis.

Accordingly, active components may include any drug designed to block pain receptors (i.e., lidocaine, novacaine, Marcaine, etc.), analgesics, or any other drugs eliciting an anti-inflammatory response (e.g., cortisone, naxoprene, ibuprofen, etc.), antibiotic/antimicrobial agents (for example, the release of metal cations as an antimicrobial function), immunostimulators or immunoinhibitors, enzymes (including, but not limited to, osteogenic promoters, cartilage stimulating enzymes, growth factors, and hyaluronic acid synthase), anticoagulants (e.g., thrombotic promoters or inhibitors), diagnostic tools (e.g., immunofluorescence markers or radioactive isotopes), and live cell cultures that produce any of the above.

Drugs which may be employed as active components in accordance with the present invention may include non-proteinaceous as well as proteinaceous drugs. Non-proteinaceous drugs may encompass compounds such as, for example, 5-FU, mitomycin C, daunorubicin, vinblastine, AZT, hormones, and other substances. Other non-proteinaceous active components include, but are not limited to, analgesics, anorexics, anthelmintics, antibacterials, anticonvulsants, antifungals, antidepressants, antibiotics, antihistamines, antiulcer drugs, antihypertensives, bronchodilators, immunosuppressants, antiinflammatories and blood glucose lowering agents.

Proteinaceous drugs may include immunomodulators and other biological response modifiers which are involved in modifying the immune response in such manner as to enhance a desired therapeutic effect. Examples of biological response modifiers include, but are not limited to, such compounds as lymphokines, for example, tumor necrosis factor, interleukins, lymphotoxin, macrophage activating factor, migration inhibition factor, colony stimulating factor, and interferons. Interferons which may be used include, but are not limited to, alpha-interferon, beta-interferon, and gamma-interferon and their subtypes. In addition, peptide or polysaccharide fragments derived from these proteinaceous drugs, or independently, may also be incorporated. Other biological response modifiers include vaccines wherein a foreign substance, usually a pathogenic organism or some fraction thereof, is used to modify the host immune response with respect to the pathogen to which the vaccine relates. Other substances which can act as proteinaceous drugs are also fully contemplated.

Radioisotopes may also be utilized as active components in conjunction with the present invention. Examples of radioisotopes include, but are not limited to, $^{125}I$, $^{131}I$, $^{90}Y$, $^{67}Cu$, $^{212}Bi$, $^{211}At$, $^{212}Pb$, $^{47}Sc$, $^{109}Pd$ and $^{188}Re$. Lectins, proteins usually isolated from plant material which bind to specific sugar moieties, may also be utilized as active components. Many lectins are also able to agglutinate cells and stimulate lymphocytes. Other active components which can be utilized include, for example, growth factors, collagen crosslinking inhibitors such as β-aminopropeonitrile or cis-4-hydroxyproline, matrix inhibitors, antibodies, cytokines, integrins, thrombins, thrombin inhibitors, proteases, anticoagulants, glycosaminoglycans, lipids, (lipo)polysaccharides, hormones, proteins, antibiotics, and cytostatics.

Other active components are also fully contemplated. The concentration of active component utilized will vary with the nature of the component, its physiological role, and the desired therapeutic effect. Examples, without limitation, of desirable medical effects which can be attained through the use of active components are chemotherapy, antibiotic therapy, birth control, and regulation of metabolism. The desired concentration in a particular instance for a particular active component is readily ascertainable by one of skill in the art. It is also understood that the active component incorporated within prosthesis 100 may provide a function outside of the body location in which prosthesis 100 is implanted. For example, insulin may be secreted from a prosthesis located in the knee joint which may then be utilized in other parts of the body.

Prosthesis 100 according to the present invention may support the incorporation and proliferation of cell cultures including, but not limited to, endothelial cells, muscle cells, fibroblasts, and other connective tissue cells. Prostheses modified by such cell lines may be better able to adapt and adjust to changing physical and physiological conditions in the body. These cellular lines may be incorporated into the prosthesis according to the present invention after it has been produced via standard cell culture protocol generally known in the art. For example, cells may be introduced by direct topical seeding and incubation in cell culture medium.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A unicompartmental knee prosthesis for surgical implantation into a knee joint compartment between a femoral condyle and its corresponding tibial plateau, the prosthesis comprising:
  a body free of any means of fixation within the knee joint compartment, the body including a bottom face, an opposed top face, and a peripheral edge extending between the top and bottom face, the body including a pump structure having a top member and a bottom member which are movable with respect to one another, the pump structure disposed within and surrounded by the body, the pump structure configured to store and release an active component therefrom upon relative movement of the top and bottom members.

2. The prosthesis according to claim 1, wherein the body includes piezoelectric crystals embedded therein.

3. The prosthesis according to claim 1, wherein the body has a generally elliptical shape in plan.

4. The prosthesis according to claim 1, further comprising an inner material disposed between the top and bottom members, the inner material configured to store the active component.

5. The prosthesis according to claim 1, wherein the pump structure includes holes therein for releasing the active component.

6. The prosthesis according to claim 1, wherein the top and bottom members nest within one another.

7. The prosthesis according to claim 1, wherein the body has a first portion and at least one second portion, wherein the at least one second portion is configured to store and release at least one active component without degradation of the mechanical function of the prosthesis.

8. The prosthesis according to claim 7, wherein the second portion is generally centrally located and surrounded by the first portion.

9. The prosthesis according to claim 7, wherein the at least one second portion is generally peripherally located and surrounds the first portion.

10. The prosthesis according to claim 7, wherein the second portion includes a load bearing surface of the prosthesis.

11. The prosthesis according to claim 7, wherein the second portion includes a non-load bearing surface.

12. The prosthesis according to claim 11, wherein the second portion is disposed along the peripheral edge.

13. The prosthesis according to claim 12, wherein the peripheral edge includes an indentation along at least a portion thereof for storing and releasing the active component.

14. The prosthesis according to claim 7, wherein the second portion includes a reservoir for storing the active component.

15. The prosthesis according to claim 7, wherein the second portion includes bleed holes for releasing the active component.

16. The prosthesis according to claim 7, wherein the second portions are constructed from different materials.

17. The prosthesis according to claim 7, wherein the at least one second portion is configured for releasing the active component sequentially.

18. The prosthesis according to claim 7, wherein the at least one second portion is configured to release different active components.

19. The prosthesis according to claim 7, wherein the at least one second portion includes a pore size specificity to function as an osmotic membrane.

20. The prosthesis according to claim 7, wherein the first portion is configured to store and release an active component.

21. The prosthesis according to claim 1, wherein the active component is replenished from outside of a skin surface.

22. The prosthesis according to claim 1, wherein the active component is released via diffusion from the body.

* * * * *